(12) United States Patent
Lu et al.

(10) Patent No.: US 7,915,318 B2
(45) Date of Patent: Mar. 29, 2011

(54) AQUEOUS ROMP-BASED MONOLITH MATERIALS AND METHODS FOR MAKING

(75) Inventors: Su Lu, Shanghai (CN); Liangliang Qiang, Shanghai (CN); Yanrong Zhu, Shanghai (CN); Zhida Pan, Shanghai (CN)

(73) Assignee: General Electric Company, Niskayuna, NY (US)

( * ) Notice: Subject to any disclaimer, the term of this patent is extended or adjusted under 35 U.S.C. 154(b) by 213 days.

(21) Appl. No.: 12/207,055

(22) Filed: Sep. 9, 2008

(65) Prior Publication Data
US 2010/0063200 A1    Mar. 11, 2010

(51) Int. Cl.
C08F 2/44 (2006.01)
B01J 20/26 (2006.01)
C08F 4/80 (2006.01)

(52) U.S. Cl. .......... 521/93; 521/124; 523/212; 524/518; 524/806; 524/807; 524/808; 524/809; 524/812; 524/815; 524/817; 524/852; 524/853; 502/402

(58) Field of Classification Search ................ 523/212; 524/518, 852, 853, 806, 807, 809, 812, 815, 524/817; 502/402; 521/93, 124
See application file for complete search history.

(56) References Cited

U.S. PATENT DOCUMENTS

| 6,416,663 | B1 | 7/2002 | Miroslav |
| 2002/0055598 | A1 | 5/2002 | Lynn et al. |
| 2006/0021939 | A1 | 2/2006 | Mallet et al. |
| 2006/0054543 | A1 | 3/2006 | Petro et al. |
| 2006/0065600 | A1 | 3/2006 | Sunkara et al. |
| 2007/0095667 | A1 | 5/2007 | Lau |
| 2007/0135304 | A1 | 6/2007 | Walter et al. |
| 2007/0144972 | A1 | 6/2007 | Bonn et al. |
| 2007/0215547 | A1 | 9/2007 | O'Gara |

FOREIGN PATENT DOCUMENTS

WO    WO2005123737    12/2005

OTHER PUBLICATIONS

Sinner et al, A New Class of Continuous Polymer Supports Prepared by Ring-Opening Metathesis Polymerization: A Straight forward Route to Functionalized Monoliths, Macromolecules 2000, 33, 5777-5786.*

(Continued)

Primary Examiner — Fred M Teskin
(74) Attorney, Agent, or Firm — Eileen W. Gallagher (57) ABSTRACT

A water soluble ROMP catalyst, which has high catalytic efficiency for ring opening metathesis is use in the preparation of polymeric blends for use in monolithic columns. In one embodiments a method for making a polymeric blend is discolosed comprising reaction of a water-soluble ROMP catalyst with a norbornene-substituted cycloolefin polymer or a polynorbornene polymer precursor, and wherein the contacting occurs in an aqueous or polar solvent in the presence of a solid support. In another embodiment a monolithic bed is disclosed comprising the water-soluble ROMP catalyst immobilized on a surface of a solid support. Also disclosed is a monolithic bed comprising: a polymer blend, the polymer blend produced from contacting a water soluble ROMP catalyst with a norbornene-substituted cycloolefin polymer or a polynorbornene polymer precursor; and wherein the contacting occurs in an aqueous or polar solvent in the presence of a solid support.

16 Claims, 2 Drawing Sheets

SIP process

OTHER PUBLICATIONS

Lubbad et al, Monolithic High-Performance SEC Supports Prepared by ROMP for High-Throughput Screening of Polymers, Macromol. Rapid Commun., 2002, 23, 617-621.*

Eder, Karoline et al., "Surface-Functionalized, Ring-Opening Metathesis Polymerization-Derived Monoliths for Anion-Exchange Chromatography", Macromol. Rapid Commun, 2007, 28, 2029-2032.

Sinner, Frank et al., "Ring-Opening Metathesis Polymerization: Access to a New Class of Functionalized, Monolithic Stationary Phases for Liquid Chromatography", Angew. Chem. Int. Ed. 2000, 39, No. 8, 1433-1436.

Buchmeiuser, M., "Applications of Metathesis in Heterogeneous Catalysis and Separation Sciences", Journal of Molecular Catalysis A: Chemical vol. 190, Issues 1-2, Dec. 2, 2002, pp. 1-2.

Lubbad, S. et al., "Metathesis Polymerization-Derived Monolithic Membranes for Solid-Phase Extraction Coupled with Diffuse Reflectance Spectroscopy", Journal of Chromatography A, vol. 1109, Issue 1, Mar. 17, 2006, pp. 1-3.

Buchmeiser, M., "Polymeric Monolithic Materials: Syntheses, Properties, Functionalization and Applications", Polymer, vol. 48, Issue 8, Apr. 5, 2007, pp. 1-3.

U.S. Appl. No. 11/680,646, filed Mar. 1, 2007, "Composition, Device and Associated Method".

U.S. Appl. No. 11/759,333, filed Jun. 7, 2007, "Composition and Associated Method".

* cited by examiner

AQUEOUS ROMP-BASED MONOLITH MATERIALS AND METHODS FOR MAKING

BACKGROUND

Chromatography columns packed with microparticulate sorbents have been widely applied as separation media. Despite many advantages, such microparticulate sorbents have limitations such as large void volume, slow mass diffusion, and the need for end frits to support and retain the microparticulate sorbents, which results in a non-homogeneous column. Monolithic chromatography beds are proposed to alleviate the problem of restricted mass transfer and eliminate the need for end frits.

Monolithic chromatography beds are porous, uniform blocks taking the form of the containment volume. Generally, monolithic chromatography beds are classified as organic polymer-based or silica-based materials. Most organic polymer-based beds are prepared by radical polymerization such as polymerization of methacrylates and poly(styrene-co-divinylbenzene). In these instances a fused silica capillary or column is filled with a polymerization mixture and radical polymerization initiated through heating. When the polymerization is complete, unreacted components may be removed physically or by electrosomotic flow. The porosity of the polymer can be partially controlled by the degree of cross linking and the amount of organic solvent used as pores are formed by the removal of the organic solvent.

Silica-based monolithic beds are typically prepared using an acid-catalyzed sol-gel process, which involves hydrolysis, condensation reactions and polycondensation of silica alkoxide precursors. Commonly used precursors are tetraethoxysilanes(TEOS) and tetramethoxysilanes (TMOS). Preparation of the beds involves mixing the precursors prior to introduction into a capillary column and a progenic reagent is added such as polyethylene glycol or poly(ethylene) oxide. The ratio of progenic reagent and silica precursors controls pore size.

Monolithic chromatography beds are used in bioanalytical assays due to high rates of mass transfer and permeability of the pores to large molecules. Thus separation of proteins, oligonucleotides, DNA, virus, bacteria or microorganisms can be achieved. Immunoaffinity separations based on antigen-antibody reactions have also been achieved. Columns based on methacryate-co-ethylene dimethacrylate (GMA-EDMA) are commercially available which contain chemically reactive epoxy groups, which can react with amino groups contained in the biological agent.

The possibility of ROMP-based (ring opening metathesis polymerization). monolithic materials and the corresponding separation efficiency in protein separation have been demonstrated. However, the ROMP-based monolithic material uses organic solvents such as isopropanol. The use of organic solvents is costly and adds to environmental concerns. Therefore the development of aqueous ROMP-based monolith chromatography media is desirable but has been limited by the lack of a highly reactive water-soluble ROMP catalyst.

BRIEF DESCRIPTION

Disclosed herein is a novel ROMP catalyst, which has high catalytic efficiency for ring opening metathesis polymerization in aqueous solutions involving water soluble cycloolefins and its use in the preparation of monolithic columns.

In one embodiments a method for making a polymeric blend suitable for use as a monolithic material comprises contacting a composition having formula (I)

with a norbornene-substituted cycloolefin polymer or a polynorbornene polymer precursor, and wherein the contacting occurs in an aqueous or polar solvent in the presence of a solid support and further wherein "a" and "b" are independently integers from 1 to 3, with the proviso that "a+b" is less than or equal to 5, M is ruthenium or osmium, X is independently at each occurrence an anionic ligand, $R^1$ is hydrogen, an aliphatic radical, a cycloaliphatic radical, or an aromatic radical, and $R^2$ is hydrogen, an aliphatic radical, a cycloaliphatic radical, or an aromatic radical, with a norbornene-substituted cycloolefin polymer or a polynorbornene polymer precursor, and wherein the contacting occurs in an aqueous or polar solvent in the presence of a solid support.

In another embodiment of the invention, a monolithic bed is disclosed comprising a solid support, and a composition of formula (I) immobilized on a surface of the solid support.

In accordance with another embodiment, a monolithic bed is disclosed comprising: a polymer blend, the polymer blend produced from contacting a composition having formula (I) with a norbornene-substituted cycloolefin polymer or a polynorbornene polymer precursor; and wherein the contacting occurs in an aqueous or polar solvent in the presence of a solid support and wherein the solid support optionally contains a porogen.

DETAILED DESCRIPTION

The following detailed description is exemplary and not intended to limit the invention of the application and uses of the invention. Furthermore, there is no intention to be limited by any theory presented in the preceding background of the invention of the following detailed description of the figures.

Definitions

As used herein the term "cycloolefin" refers to a non-aromatic cyclic ring having at least one carbon-carbon double bond in the cyclic ring. A cyclic olefin may comprise: a strained cyclic structure (for example, norbornene), one or more heteroatoms (for example, oxanorbornene), at least two carbon-carbon double bonds (for example, norbornadiene), and two or more cyclic rings that may be fused with each other (for example, dicyclopentadiene). A cycloolefin may be substituted with at least one ionic group, and the ionic group comprises one or more of phosphite, phosphate, sulfite, sulfate, sulfonate, nitrite, nitrate, azide, carboxylate, ammonium, quaternary ammonium, phosphonium, quaternary phosphonium, imidazolium, pyridinium, or sulfonium.

As used herein the term "polymer precursor" refers to materials that are capable of undergoing polymerization. The "polymer precursor" may comprise a norbornene-substituted cycloolefin or a polynorbornene.

As used herein the term "ring opening metathesis polymerization" (ROMP) refers to a polymerization method in which cyclic olefins, such as norbornene or cyclopentene, are polymerized by alkene metathesis. The polymerization involves redistribution of alkene bonds and opening of the cycloolefinic structure.

As used herein, the term "transition metal" refers to an element whose atom has an incomplete d sub-shell, or which can give rise to cations with an incomplete d sub-shell. As used herein, the term "Group (VIII) transition metal" refers to transition metals in the Group (VIII) of the periodic table. A Group (VIII) transition metal may comprise ruthenium (Ru) or Osmium (Os).

Provided herein are methods and apparatus for the preparation of monolithic chromatography beds by water-based ROMP. Representative methods and apparatuses for ROMP are described in co-owned U.S. patent application Ser. Nos. 11/680,646 and 11/759,333, which are incorporated herein by reference.

A metal-complex (for example, a ruthenium alkylidine complex) may catalyze a ROMP of a cycloolefin. For activity in an aqueous or polar environment, the metal-complexes employed as metathesis catalysts needs to have catalytic activity in an aqueous or polar environment and for the cycloolefin to be soluble in an aqueous or polar environment.

In one embodiment, a method is provided that comprises a method for preparation of a monolithic chromatography bed using a novel metal complex, which has shown high catalytic efficiency for ring opening metathesis polymerization in aqueous solutions. The bed is prepared by synthesizing a norbornene-substituted cycloolefin polymer precursor or a polynorbornene polymer precursor having aqueous solubility. The norbornene-substituted cycloolefin polymer precursor or a polynorbornene polymer precursor is mixed together with a metal complex in an aqueous or polar solvent in an amount sufficient for the metal complex and the ionic-group substituted polymer precursor to form a homogeneous solution. The metal complex initiates a ring opening metathesis polymerization reaction when contacted to the polymer precursor. A ring-opening metathesis reaction of the polymer precursor refers to a chemical reaction involving redistribution of alkene bonds and opening of the cycloolefinic structure. The opening of the cycloolefinic structure leads to polymerization.

In one embodiment, the metal complex may be prepared by contacting a composition having a formula (I)

wherein "a" and "b" are independently integers from 1 to 3, with the proviso that "a+b" is less than or equal to 5, M is ruthenium or osmium, X is independently at each occurrence an anionic ligand, L is independently at each occurrence a neutral electron donor ligand, R1 is hydrogen, an aliphatic radical, a cycloaliphatic radical, or an aromatic radical, and R2 is hydrogen, an aliphatic radical, or an aromatic radical; with a norbornene-substituted cycloolefin polymer precursor or a polynorbornene polymer precursor.

In one embodiment, at least one L in formula (I) may comprise a phosphine ligand. In one embodiment, at least one L in formula (I) may comprise P (cyclohexyl)$_3$, P(cyclopentyl)$_3$, P(isopropyl)$_3$, or P(phenyl)$_3$. In one embodiment, at least one L in formula (I) may comprise P(cyclohexyl)$_3$. In one embodiment, at least one L in formula (I) may comprise a monodentate pyridine ligand, which is unsubstituted or substituted. In one embodiment, at least one L in formula (I) may comprise a bromine-substituted monodentate pyridine ligand. In one embodiment, at least one L in formula (VI) may comprise a N-heterocyclic carbene ligand (NHC).

In one embodiment, $R^2$ in formula (I) may comprise an aromatic radical. In one embodiment, $R^2$ in formula (I) may comprise a substituted or an unsubstituted benzyl radical. In one embodiment, at least one X in formula (I) may comprise a halide. In one embodiment, at least one X in formula (I) may comprise a chloride.

In one embodiment, a composition having a formula (I) may comprise Bis(tricyclohexylphosphine) benzylidine ruthenium(IV) chloride (CAS No. 172222-30-9), 1,3-Bis(2,4,6-trimethylphenyl)-2-imidazolidinylidene)dichloro (phenylmethylene)(tricyclohexylphosphine)ruthenium(CAS No. 246047-72-3), 1,3-Bis(2,4,6-trimethylphenyl)-2-imidazolidinylidene)dichloro(phenylmethylene)(di-3-bromopyridine)ruthenium, or 1,3-Bis-(2,4,6-trimethylphenyl)-2-imidazolidinylidene)dichloro(o-isopropoxyphenylmethylene) ruthenium (CAS No. 301224-40-8).

In one embodiment, a suitable norbornene-substituted cycloolefin polymer precursor or a polynorbornene polymer precursor for contacting with formula (I) may comprise at least one of monomeric species, oligomeric species, mixtures of monomeric species, mixtures of oligomeric species, polymeric species, mixtures of polymeric species, partially-cross linked species, or mixtures of partially-cross linked species.

In one embodiment, a suitable norbornene-substituted cycloolefin polymer precursor for contacting with formula (I) may refers to a strained cyclic structure, capable of being dissolved or suspended in an aqueous or polar solvent, and having a formula (II) or (III)

wherein "w" may be 0, 1, 2, or 3;
"x" may be 0 or 1;
"y" may be 1 or 2;
$R^3$ may be, independently at each occurrence, hydrogen, a halogen atom, an aliphatic radical, a cycloaliphatic radical, an aromatic radical, an alkoxy group, a hydroxy group, an ether group, an aldehyde group, a ketone group, a silanyl group, a phosphanyl group, an amine group, a nitro group, or a divalent bond linking two carbon atoms;
$R^4$ may be, independently at each occurrence, an ionic group, wherein the ionic group comprises one or more of phosphite, phosphate, sulfite, sulfate, sulfonate, nitrite, nitrate, azide, carboxylate, ammonium, quaternary ammonium, phosphonium, quaternary phosphonium, imidazolium, pyridinium, or sulfonium;

R⁶ may be an aliphatic or an aromatic cyclic ring; and

Z may be C(R⁷)₂, C=C(R⁷)₂, Si(R⁷)₂, O, S, N—R⁷, P—R⁷, B—R⁷, or As—R⁷, wherein R⁷ may be independently at each occurrence hydrogen, an aliphatic radical, a cycloaliphatic radical, or an aromatic radical. Aliphatic radical, cycloaliphatic radical, and an aromatic radical are as defined hereinabove.

In one embodiment, at least one of R³ or R⁴ may comprise a peptide group, a carbohydrate group, or derivatives of the foregoing. In one embodiment, at least one of R³ or R⁴ may comprise a derivative of glucose. In one embodiment, at least one of R³ or R⁴ may comprise a carboxylic acid derivative of glucose. In one embodiment, at least one of R³ or R⁴ may comprise a gluconate group.

In one embodiment at least one of R³ or R⁴ may be substituted with at least one ionic group, and the ionic group comprises one or more of phosphite, phosphate, sulfite, sulfate, sulfonate, nitrite, nitrate, azide, carboxylate, ammonium, quaternary ammonium, phosphonium, quaternary phosphonium, imidazolium, pyridinium, or sulfonium In one embodiment, a suitable polymer precursor may comprise a polymer having one or more structural units derived from a norbornene cycloolefin having a formula (II) or (III) and which is capable of being dissolved or suspended in an aqueous or polar solution. In one embodiment, a suitable polynorbornene may comprise structural units having a formula (IV) or (V):

wherein "w", "x", "y", R³, R⁴, R⁵, R⁶ and Z are as defined hereinabove;

"n" may be an integer of from 1 to 100;

"p" is an integer in a range of from about 1 to about 100; and

D is a divalent aromatic radical. In one embodiment, D may comprise a divalent aromatic radical and one or more divalent aliphatic radical —R⁸—, —R⁸O—, —R⁸CO₂—, —R⁸OCO—, R⁸CO₂ R⁸—, —R⁸CO₂NR⁹—, —R⁸N R⁹CO—, —R⁸CONR⁹R⁸—, or —R⁸NR⁹CO R⁸—, wherein R⁸ is a C₁-C₂₀ aliphatic radical and R⁹ is hydrogen or C₁-C₁₀ aliphatic radical. In one embodiment, D may comprise a divalent benzyl radical and one or more of the aforementioned divalent aliphatic radical.

In one embodiment, at least one of R³ or R⁴ may comprise a peptide group, a carbohydrate group, or derivatives of the foregoing. In one embodiment, at least one of R³ or R⁴ may comprise a derivative of glucose. In one embodiment, at least one of R³ or R⁴ may comprise a carboxylic acid derivative of glucose. In one embodiment, at least one of R³ or R⁴ may comprise a gluconate group.

In one embodiment at least one of R³ or R⁴ may be substituted with at least one ionic group, and the ionic group comprises one or more of phosphite, phosphate, sulfite, sulfate, sulfonate, nitrite, nitrate, azide, carboxylate, ammonium, quaternary ammonium, phosphonium, quaternary phosphonium, imidazolium, pyridinium, or sulfonium In one embodiment a, suitable polymer precursor may comprise a polymer having one or more structural units derived from a polyolefin and having a pendant norbornene cycloolefin having a norbornene cycloolefin having a formula (VI)

wherein R³ may be hydrogen, a halogen atom, an aliphatic radical, a cycloaliphatic radical, an aromatic radical, an alkoxy group, a hydroxy group, an ether group, an aldehyde group, a ketone group, a silanyl group, a phosphanyl group, an amine group, a nitro group, or a divalent bond linking two carbon atoms;

"k" is an integer in a range of about 1 to 10;

"n" is an integer in a range of from about 1 to about 100; and

Z may be C(R⁷)₂, C=C(R⁷)₂, Si(R⁷)₂, O, S, N—R⁷, P—R⁷, B—R⁷, or As—R⁷, wherein R⁷ may be independently at each occurrence hydrogen, an aliphatic radical, a cycloaliphatic radical, or an aromatic radical. Aliphatic radical, cycloaliphatic radical, and an aromatic radical are as defined hereinabove.

Catalytic efficiency or initiator efficiency of the metal complex prepared by contacting a composition having a formula (I) with a norbornene-substituted cycloolefin polymer precursor or a polynorbornene polymer precursor may be affected by one or more of the reaction conditions (for example, temperature, solvent, and the like), number of ligands, type of ligands, or type of alkylidene ligand substituents. Catalytic efficiency or initiator efficiency may be measured as the turnover frequency (TOF) of the polymer precursor. Turnover frequency refers to the number of polymer precursors converted by the metal complex in one second and may vary from a polymer precursor turnover frequency in a range of greater than about 10 per second to a polymer precursor turnover frequency in a range of greater than about 2000 per second.

The polymer precursor may be homogeneous, producing a homopolymer or a mix of one or more polymer precursors producing a copolymer. The polymer formed may be linear, branched, or cross linked. In one embodiment, the conversion of the polymer precursor may be complete, that is, the reaction product may be free of any unreacted polymer precursor. In an alternative embodiment, the conversion of the polymer precursor may be incomplete, that is, the reaction product may comprise unreacted polymer precursor. In one embodiment, the conversion of the polymer precursor may be in a range that is greater than about 50 weight percent. In one embodiment, the conversion of the polymer precursor may be in a range of from about 50 weight percent to about 60 weight percent, from about 60 weight percent to about 70 weight percent, from about 70 weight percent to about 80 weight percent, from about 80 weight percent to about 90 weight percent, or from about 90 weight percent to about 100 weight percent.

In one embodiment, a method is provided comprising contacting a composition having a formula (I), with a norbornene-substituted cycloolefin polymer precursor or a polynorbornene polymer precursor. In one embodiment the individual species, formula (I) and the norbornene-substituted cycloolefin polymer precursor or polynorbornene polymer precursor, are in an aqueous solution. In alternative embodiments, polar solutions maybe used or mixtures thereof. A polar solvent may comprise one or more of water, methanol, tetrahydrofuran, ethanol, isopropanol, ethylene glycol, 1,4-dioxane, morpholine, dimethyl sulfoxide, dimethyl formamide, acetone, acetonitrile, nitrile, nitromethane, pyridine, dimethyl pyridine, or N-methyl pyrrolidinone.

A polar solvent may be present in an amount sufficient that the composition is a slurry (a suspension) or a solution. In one embodiment, a polar solvent may be present in an amount sufficient that the composition is a solution. In one embodiment, a polar solvent may be present in an amount sufficient that the composition may not phase separate at room temperature. In one embodiment, a polar solvent may be present in an amount sufficient that the composition may be substantially transparent to visible light. The term "transparent" may refer to allowing at least 50 percent, at least 80 percent, or at least 90 percent, of incident light in the visible wavelength range having an angle of incidence of less than about 10 degrees to be transmitted.

Solubility of a metal complex in a polar solvent may be affected by one or more of the type of ionic groups, type of polar solvent, number of ionic groups in the metal complex, molecular weight of the metal complex, concentration of metal complex in the polar solvent, or temperature. In one embodiment, solubility of a metal complex in the polar solvent may be adjusted by varying the number of ionic groups present in the metal complex. In one embodiment, solubility of a metal complex in the polar solvent may be adjusted by varying molecular weight through varying chain length or "n". In one embodiment, "n" may be in a range of from about 10 to about 20 and the metal complex may form a solution in the polar solvent.

Figure 1:
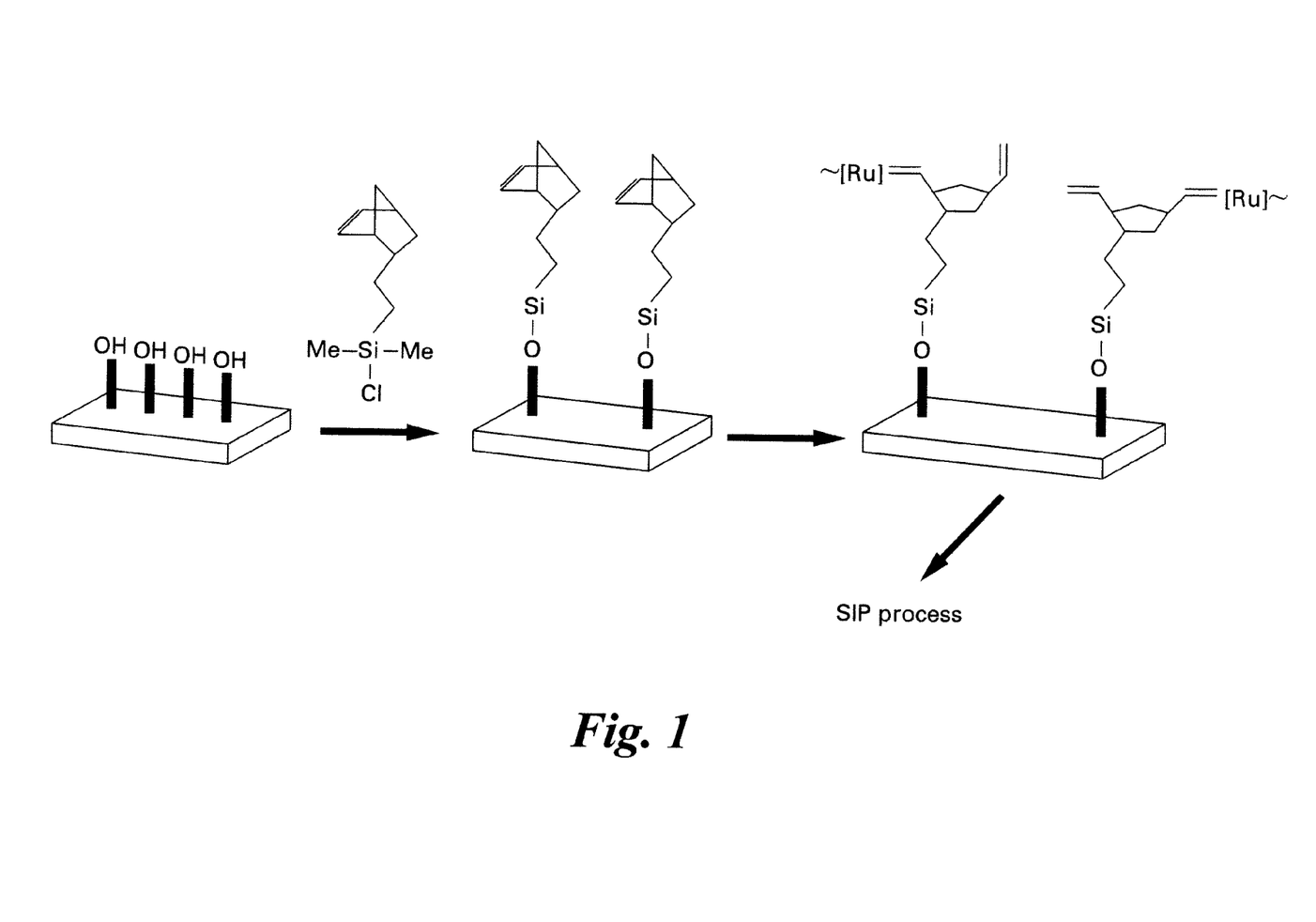
FIG. 1 depicts preparation of a ROMP catalyst modified surface.

In one embodiment, as shown in FIG. 1, the norbornene-substituted cycloolefin polymer precursor or a polynorbornene polymer precursor may be immobilized on a solid surface prior to contacting with the metal complex. The metal complex reacts with the polymer precursor and is immobilized while retaining catalytic activity. A norbornene monomer solution may then be added which undergoes polymerization in the presence of the metal complex. In one embodiment, the norbornene monomer solution may be added directly after the metal complex is immobilized on the solid surface. In another embodiment, the norbornene monomer solution may be added at a later date wherein the immobilized metal complex is prepared for later use.

A solid support may comprise a polymeric, a silica, or a metallic material. The metal complex having formula may be immobilized on the solid support by physical adsorption, by chemical bond formation, or by combinations thereof. The solid support serves as a reaction vessel producing a three-dimensional network that can be utilized as a monolithic chromatography bed.

The solid support may have vastly different dimensions In one embodiment the solid support may comprise traditional laboratory glassware such as a beaker or a small diameter capillary tube (microliter range volume), a tubular column, a microtiter plate, a bead, a filter, a test strip, a slide, a cover slip, a chip, a nanoparticle, or a test tube. In one embodiment, the solid support may be sized to allow for commercial size separation and may comprise pipes or tubes fabricated from glass, metal or plastic materials. The pipes or tubes may vary in diameter or length to control velocity of a material passing through the fabricated monolithic chromatography bed. In one embodiment, the solid support may be pretreated to increase the affinity of the metal complex to the solid surface and therein increase the concentration of binding sites on the solid support. Pretreatment may comprise washing with alkali or acid solutions.

In one embodiment the porosity of the monolithic chromatography bed may be controlled by at least one of the degree of cross-linking of the polymer precursor and the polymer precursor's chain length. or "n". Chain length may be controlled by varying one or more of molar ratio of the composition having formula (I) and the polymer precursor, the reaction temperature, or the time duration of reaction. In one embodiment, a method may comprise controlling the chain length or "n" by varying a molar ratio of the composition having formula (I) and the polymer precursor. In one embodiment, a molar ratio of composition having formula (I) and the polymer precursor may be varied to control "n" to be in a range of from about 10 to about 20.

In one embodiment the porosity of the monolithic chromatography bed may be controlled by evaporation of removal of the solvent from the bed. In one embodiment an organic solvent, at least partially miscible with a polar solvent may be used in the formation of the column and the organic solvent removed by vacuum or pressure.

In one embodiment a porogen may be used to create pores in the monolithic chromatography bed. In one embodiment the porogen may be a polymer or particles that are inert to the monolithic reagents. Pore size may be determined by the size of the porogen particle and wherein the porogen may be a polymer by the molecular weight of the polymer. In one embodiment, after the monolithic chromatography bed is cast, a suitable leaching solvent may be used to dissolve and remove the porogen.

In one embodiment, a composition may comprise a norbornene-substituted cycloolefin polymer precursor, a polar solvent, and the metal complex. A metal complex may initiate a ring-opening metathesis polymerization reaction of the norbornene-substituted cycloolefin polymer precursor. A norbornene-substituted cycloolefin polymer precursor may comprise monomeric species, oligomeric species, mixtures of monomeric species, mixtures of oligomeric species, polymeric species, mixtures of polymeric species, partially-cross linked species, mixtures of partially-cross linked cross linked species, or mixtures of two or more of the foregoing. In one embodiment, a metal complex may be particularly suitable for ring opening metathesis polymerization of a cycloolefin polymer precursor in a polar solvent, such as water. In one embodiment, a metal complex may be particularly suitable for ring opening metathesis polymerization of a hydrophilic norbornene-substituted cycloolefin polymer precursor in a polar solvent, such as water.

In one embodiment, a monolithic bed is provided. The monolithic bed may comprise a solid-support and a metal complex immobilized on a surface of the solid support. In one embodiment, a monolithic support may comprise a solid-support and a polymeric reaction product of a metal complex and a cycloolefin polymer precursor, immobilized on a surface of the solid support.

EXAMPLES

Example 1

Synthesis of Norbornene-sodium Sulfonate

Scheme 1: Synthesis of the water-soluble monomer Norbornene-sodium sulfonate 1 g of 5-norbornene-2-methanol (CAS 95-12-5) and 0.6 g of NaH (60% dispersion in mineral oil) were dissolved in 50 ml anhydrous THF. The mixture is refluxed at 80° C. overnight (at least 10 hours) after which 0.98 g of 1,3-propane sultone (CAS 1120-71-4) in 20 ml of THF was added into the mixture in 10 minutes. After further reacting 5 hours, the solvent was removed by rotary evaporation and purified by column chromatography using silica and ethyl acetate/methanol (4:1) as eluant. The product is white solid and could dissolve in water or methanol. The yielding is about 60%.

Example 2

Synthesis of Norbornene-Gluconate

Scheme 2: Synthesis of the water-soluble monomer Norbornene-gluconate 2 ml methanol was added to a 50 ml flask containing 1 g Glucolactone (Aldrich), the solid does not dissolve initially. By the addition of 0.74 g Norbornenyl-methylamine (prepared in lab by the reduction of norbornene carbonitrile with LiAlH4), it disappeared gradually within 20 minutes. The reaction proceeded overnight at room temperature. After the reaction, methanol was removed on a rotary evaporator, and the product was recrystalized from iPrOH/petroleum ether at −4° C. with a yield greater than 70%.

Experiment 3

Synthesis of the Water-soluble ROMP Catalyst

Scheme 3: Synthesis of the water-soluble ROMP catalyst (B)

5 mg Gen III Grubbs catalyst (A) was charged in a HPLC flask, degassed and purged with argon for three times. Then 50 uL of degassed dichloromethane was injected into the flask by syringe. The mixture was cooled down in a dry ice/acetone bath at −78° C. In another flask, 10 mg of norbornene sulfonate was charged and degassed and backfilled with argon three times followed by addition of 500 uL of degassed methanol. After cooled at −78° C. for 5 minutes, the norbornene sulfonate mixture was transferred into the catalyst solution. Upon mixed thoroughly under low temperature, the mixture was allowed to room temperature for 10 minutes. The yellow precipitation appeared in two minutes. After the solvent was removed under vacuum, the bright yellow water-soluble catalyst was afforded. The proton NMR spectrum shows a broad signal around 18 ppm representative of the alkylidene hydrogen of the ROMP catalyst (B).

The obtained water-soluble ROMP initiator (B) shows surprisingly high catalytic activity. After the synthesis of the complex, all organic solvents were removed, and the product was dissolved in water, a second monomer, norbornene-gluconate was added to test its activity, the solution became solid almost simultaneously and showed adherence to glassware.

Figure 2:
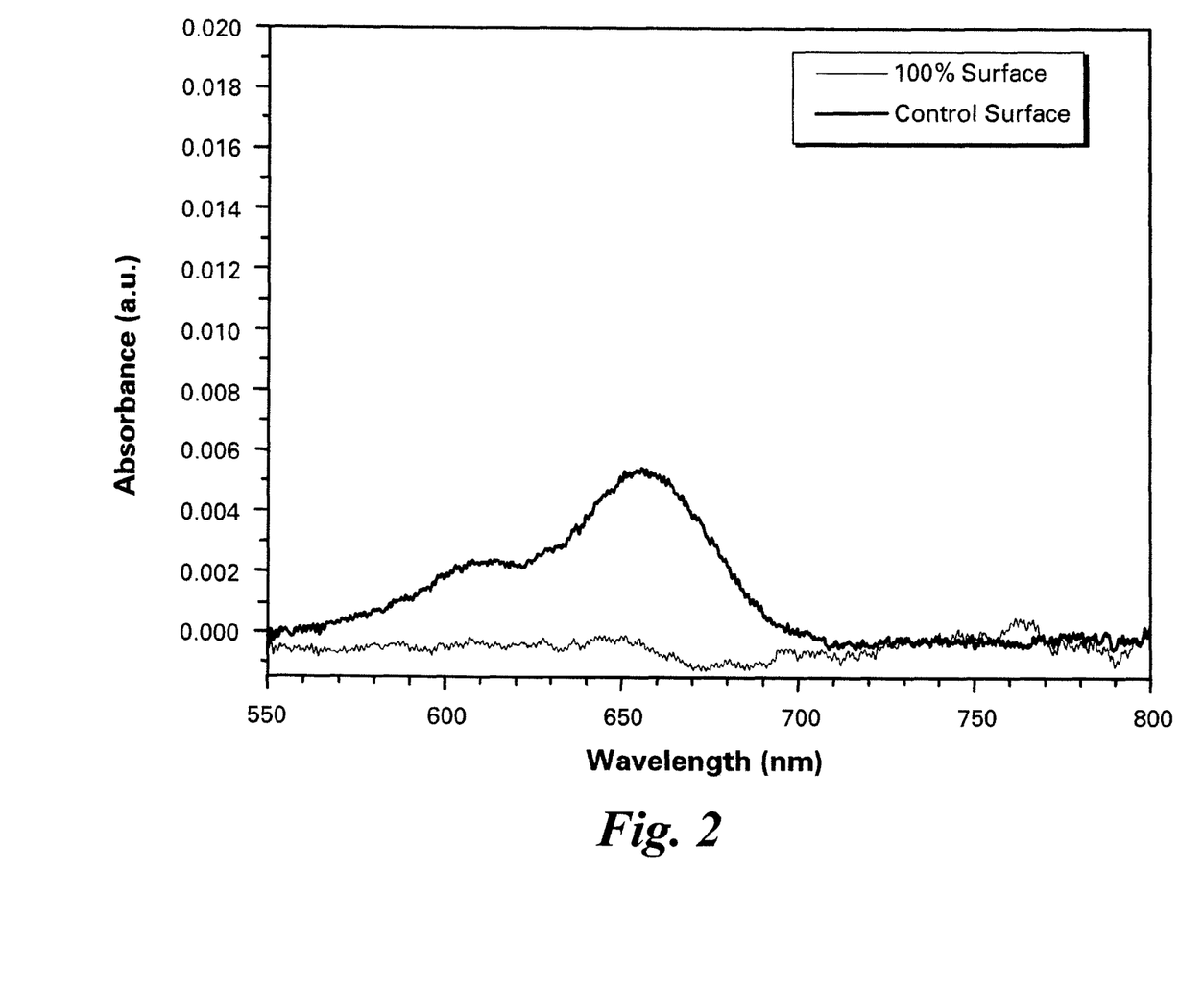
FIG. 2 depicts a UV-Visible spectra of a surface initiated polymerization (SIP) of Cy5-labeled norbornene using a ROMP catalyst.

Surface initiated polymerization (SIP) of Cy5-labeled norbornene in the presence of the water-soluble ROMP catalyst (B) occurred on the surface of a glass slide. FIG. 2 shows UV-Visible spectra of a surface initiated polymerization (SIP) of Cy5-labeled norbornene using the ROMP catalyst.

SIP may also be observed by fluorescent spectroscopy. A fluorescent-labeled monomer may be prepared by labeling a norbornene monomer with a fluoroscenin such as fluorescein isothiocyanate (FITC) prior to polymerization.

The invention claimed is:

1. A method for making a polymeric blend suitable for use as a monolithic material comprising the steps of:
   contacting a composition having formula (I)

wherein "a" and "b" are independently integers from 1 to 3, with the proviso that "a+b" is less than or equal to 5,
   M is ruthenium or osmium,
   X is independently at each occurrence an anionic ligand,
   L is independently at each occurrence a neutral electron donor ligand,
   $R^1$ is hydrogen, an aliphatic radical, a cycloaliphatic radical, or an aromatic radical, and
   $R^2$ is hydrogen, an aliphatic radical, a cycloaliphatic radical, or an aromatic radical;
   with a norbornene-substituted cycloolefin polymer or a polynorbornene polymer precursor; and
   wherein the contacting occurs in an aqueous or polar solvent in the presence of a solid support, and
   wherein the aqueous or polar solvent further contains a porogen, and
   wherein the porogen is a polymer.

2. The method of claim 1 wherein the contacting results in a ring opening methathesis polymerization reaction.

3. The method of claim 1 wherein the norbornene-substituted cycloolefin polymer or the polynorbornene polymer precursor comprises at least one of monomeric species, oligomeric species, mixtures of monomeric species, mixtures of oligomeric species, polymeric species, mixtures of polymeric species, partially-cross linked species, or mixtures of partially-cross linked species.

4. The method of claim 3 wherein the norbornene-substituted cycloolefin polymer precursor comprises structural units having a formula (II) or (III)

wherein "w" is 0, 1, 2, or 3;
   "x" is 0 or 1;
   "y" is 1 or 2;
   $R^3$ is hydrogen, a halogen atom, an aliphatic radical, a cycloaliphatic radical, an aromatic radical, an alkoxy group, a hydroxy group, an ether group, an aldehyde group, a ketone group, a silanyl group, a phosphanyl group, an amine group, a nitro group, or a divalent bond linking two carbon atoms;
   $R^4$ is an ionic group, wherein the ionic group comprises one or more of phosphite, phosphate, sulfite, sulfate, sulfonate, nitrite, nitrate, azide, carboxylate, ammonium, quaternary ammonium, phosphonium, quaternary phosphonium, imidazolium, pyridinium, or sulfonium;
   $R^6$ is an aliphatic or an aromatic cyclic ring; and
   Z is $C(R^7)_2$, $C{=}C(R^7)_2$, $Si(R^7)2$, O, S, $N{-}R^7$, $P{-}R^7$, $B{-}R^7$, or $As{-}R^7$, wherein $R^7$ is hydrogen, an aliphatic radical, a cycloaliphatic radical, or an aromatic radical.

5. The method as defined in claim 3 wherein the polynorbornene polymer precursor structural units have formula (IV), (V), or (VI):

wherein "w" is 0, 1, 2, or 3;
   "x" is 0 or 1;
   "y" is 1 or 2;
   $R^3$ is hydrogen, a halogen atom, an aliphatic radical, a cycloaliphatic radical, an aromatic radical, an alkoxy group, a hydroxy group, an ether group, an aldehyde group, a ketone group, a silanyl group, a phosphanyl group, an amine group, a nitro group, or a divalent bond linking two carbon atoms;
   $R^4$ is an ionic group, wherein the ionic group comprises one or more of phosphite, phosphate, sulfite, sulfate, sulfonate, nitrite, nitrate, azide, carboxylate, ammonium, quaternary ammonium, phosphonium, quaternary phosphonium, imidazolium, pyridinium, or sulfonium;
   $R^6$ is an aliphatic or an aromatic cyclic ring; and
   Z is $C(R^7)_2$, $C{=}C(R^7)_2$, $Si(R^7)2$, O, S, $N{-}R^7$, $P{-}R^7$, $B{-}R^7$, or $As{-}R^7$, wherein $R^7$ is hydrogen, an aliphatic radical, a cycloaliphatic radical, or an aromatic radical;

"k" is an integer in a range of from about 1 to 10;

"n" is an integer in a range of from about 1 to about 100;

"p" is an integer in a range of from about 1 to about 100; and

D is a divalent radical, wherein the divalent radical comprises one or more of a aromatic radical or a aliphatic radical —$R^8$—, —$R^8O$—, —$R^8CO_2$—, —$R^8OCO$—, $R^8CO_2R^8$—, —$R^8CO_2NR^9$—, —$R^8NR^9CO$—, —$R^8CONR^9R^8$—, or —$R^8NR^9COR^8$—, wherein $R^8$ is a $C_1$-$C_{20}$ aliphatic radical and $R^9$ is hydrogen or $C_1$-$C_{10}$ aliphatic radical.

6. The method as defined in claim 5 wherein n+p is an integer from about 10 to about 20.

7. The method as defined in claim 1 wherein the polar solvent comprises at least one of water, methanol, tetrahydrofuran, ethanol, isopropanol, ethylene glycol, 1,4-dioxane, morpholine, dimethyl sulfoxide, dimethyl formamide, acetone, acetonitrile, nitrile, nitromethane, pyridine, dimethyl pyridine, N-methyl pyrrolidinone, and mixtures thereof.

8. The method as defined in claim 1 wherein the solid support solid comprises a polymeric, silica, or metallic material.

9. The method as defined in claim 8 wherein the solid support is pretreated to increase the affinity of composition having formula (I) to the solid support.

10. The method as defined in claim 9 wherein pretreatment comprises washing the solid support with alkali or acid solutions.

11. A monolithic bed comprising;

a solid support; and a composition of formula (I)

wherein "a" and "b" are independently integers from 1 to 3, with the proviso that "a+b" is less than or equal to 5, M is ruthenium or osmium, X is independently at each occurrence an anionic ligand, L is independently at each occurrence a neutral electron donor ligand, $R^1$ is hydrogen, an aliphatic radical, a cycloaliphatic radical, or an aromatic radical, and $R^2$ is hydrogen, an aliphatic radical, a cycloaliphatic radical, or an aromatic radical; and wherein the composition of formula (I) is immobilized on the surface of the solid support and one or more porogens;

wherein the one or more porogens comprises a polymer.

12. The monolithic bed of claim 11 wherein the solid support comprises a polymeric, silica, or metallic material.

13. The monolithic bed of claim 11 wherein the composition of formula (I) is immobilized on the solid support by physical adsorption, by chemical bond formation, or by combinations thereof.

14. A monolithic bed, made for making a polymeric blend suitable for use as a monolithic material and using the method of claim 1, comprising:

a solid support; and the polymer blend adhered to the solid support.

15. The monolithic bed of claim 14 wherein the solid support comprises a polymeric, silica, or a metallic material.

16. The monolithic bed of claim 15 wherein the polymer blend adheres to the solid support by physical adsorption, by chemical bond formation, or by combinations thereof.

* * * * *